(12) United States Patent
Lavallee et al.

(10) Patent No.: US 6,491,700 B1
(45) Date of Patent: Dec. 10, 2002

(54) METHOD FOR READJUSTING MEDICAL IMAGES ON A PATIENT AND ASSOCIATED DEVICE

(75) Inventors: Stéphane Lavallee, Saint Vincent de Mercuze (FR); Sébastien Schmerber, Grenoble (FR)

(73) Assignee: Praxim, La Tronche (FR)

( * ) Notice: Subject to any disclaimer, the term of this patent is extended or adjusted under 35 U.S.C. 154(b) by 0 days.

(21) Appl. No.: 09/677,327

(22) Filed: Sep. 29, 2000

(30) Foreign Application Priority Data

Oct. 1, 1999 (FR) .......................................... 99/12525

(51) Int. Cl.⁷ ............................................... A61B 19/00

(52) U.S. Cl. ..................................................... 606/130

(58) Field of Search ......................................... 606/130

(56) References Cited

U.S. PATENT DOCUMENTS

| 4,465,069 A | 8/1984 | Barbier et al. |
| 4,617,925 A | 10/1986 | Laitinen |
| 5,474,564 A | 12/1995 | Clayman et al. |
| 5,807,252 A | 9/1998 | Hassfeld et al. |

*Primary Examiner*—Eduardo C. Robert
(74) *Attorney, Agent, or Firm*—Duane Morris, LLP (57) ABSTRACT

The present invention relates to a method for readjusting the reference frame of a three-dimensional image of a patient on the reference frame of this patient placed in a operating chamber, including the step of placing on the patient a device having a predetermined position relation with the patient's anatomic structure. The present invention also relates to various devices applicable to a wide series of patients and having a predetermined relation with the patient's anatomic structure. Thus, a device applicable to a patient's head includes an element including three anatomic bearings to bear against the forehead and the root of the nose, and a holding bar coupled to the patient's ears.

12 Claims, 6 Drawing Sheets

METHOD FOR READJUSTING MEDICAL IMAGES ON A PATIENT AND ASSOCIATED DEVICE

FIELD OF THE INVENTION

The present invention relates to the field of medical imaging applicable to computer-assisted surgery.

BACKGROUND OF THE INVENTION

A conventional equipment used for computer-assisted surgery, or more specifically computer-assisted surgical acts, includes a three-dimensional localization system that determines the positions an spatial orientations of marking means mounted on instruments, pointers, sensors, or anatomic structures, which localization system may be optical, magnetic, mechanical, ultrasonic, inertial, etc.

In this type of surgical intervention, three-dimensional images of the patient to be operated on are performed prior to the intervention. These images can be performed several days before the intervention and they are performed in the room where the medical imaging equipment (scanner, magnetic resonance MRI, etc.) is. During the surgical intervention, the pre-recorded images and the position of an intervention tool acting on the patient are desired to be simultaneously observed. The pre-recorded images thus have to be transposed to the operating reference frame. In other words, the reference frame of the pre-recorded images has to be readjusted on a reference frame linked to the patient.

For this purpose, conventionally, specific points of the patient or material structures are made to correspond with the same points or structures repeated in the pre-recorded images. Further, once this correspondence has been established once, it is desired to be able to recover it if the patient moves, if he is displaced or upon another intervention. For this purpose, a reference body, the motions of which, followed by a localization system, are determined and used to readjust the pre-recorded images on the patient, is attached to the patient.

Various reference body fastening means are possible.

In neurosurgery and in brain radiotherapy, known systems use a ring placed around the skull and on which are installed tags visible in the localization system. These generally are relatively light so-called stereotactic frames, which are attached by tightening around the head or by fastening in the cranium.

In ENT surgery, known systems use a flexible helmet that encompasses the patient's head and that is globally tightened around the head, as well as systems using a nasal bearing and pins that are placed in the ears. These two types of systems do not provide a good stability along time and can generate significant inaccuracies, especially if they are disassembled and assembled back on the patient.

In orthopedic surgery, it is known to place in the operated bone rods with screws on which the marking means are then fastened; more specifically, in spine surgery, pliers with jaws that are tightened on the spinal crests of the operated vertebras are generally placed. The marking means are then installed on these pliers. Such fastenings are rigid and invasive.

None of these fastening devices brings the reference body to come to a predetermined position with the patient's anatomic structure and, to readjust the reference of the pre-established three-dimensional images on the reference frame of the marking means, the position of the reference body with respect to the patient first has to be found, and the patient's anatomic structures then have to be readjusted on the reference frame of the reference body. This has the disadvantage of requiring localization of anatomic points of the patient and can be a source of errors. Further, if for any reason, the fastening device has to be removed from the patient, it will be necessary to resume this localization of anatomic points of the patient to determine the new relation between the position of the new location of the fastening device and the patient's anatomic structure.

Besides, fastening devices are known that follow the shape of anatomic structures.

Thus, in general radiotherapy, anatomic mattresses that follow the shape of the patient's body have been used; such mattresses, for example thermo-inflatable mattresses, in addition to the discomfort that they cause, in practice only provide a poor accuracy.

The use of made-to-measure moulds or templates for each patient such that they coincide with the external shape of an anatomic structure defined on medical images of this structure is also known. This solution has the disadvantage of requiring formation of an individualized template for each patient, which is heavy to implement and increases costs.

Dental castings to be fastened on the patient's jaw or mandible have also been used; marking means are attached on these dental castings and enable the localization system to find the position of the castings. Here again, this solution has the disadvantage of requiring an individual casting for each patient. Further, a disadvantage of this system is that the dental casting must be pressed against the teeth all along the system use and, besides, the bulk of such castings can be disturbing for certain types of surgery (oral surgery, for example) or for the placing of breathing pipes.

To perform the readjustment, prior art uses three methods.

Thus, in known methods, the reference body is placed on the patient at the time of the imaging examination. This reference body may be one of the devices described hereabove, like the nasal bearing including pins placed in the ears, or material structures, such as screws, balls, rings, stuck against the skin or inserted in a patient's bone. This reference body is easily found on the obtained images, for example by application programs. The position of the reference body must not vary and these methods have the disadvantage of having to leave, on the patient, the reference body between the imaging examination and the surgical intervention. In practice, it is often necessary to perform a new imaging examination just before the intervention.

In other known methods, the reference body is not placed on the patient during the imaging examination. These methods use a readjustment by means of a number of specific anatomic points of the patient. Upon intervention, an operator or a surgeon points at specific points of the patient with a sensor to find them with respect to the localization system. Application programs find these specific points on the images, which enables readjustment of the pre-recorded image during the intervention. The major disadvantage of such methods is that the finding of anatomic points necessarily is somewhat inaccurate. This can cause significant errors, especially in rotation.

Other more accurate methods use application programs having clouds of points belonging to two surfaces match together. A cloud of points (20 points, for example) is located by the surgeon on an anatomic surface of the patient and the readjustment between this surface and the homologous surface located on the images is performed by application programs using iterative convergence algorithms. Such methods have the disadvantage of requiring long computation times or of being rather unreliable if they do not start from an initial position close to the solution.

An object of the present invention is to provide a method for readjusting the reference frame of a three-dimensional image of a patient on the reference frame of a patient which is easy to implement.

An object of the present invention is to provide a method for readjusting the reference frame of a three-dimensional image of a patient on the reference frame of a patient, which is reliable and allows displacements of the patient.

An object of the present invention is to provide a method that does not require the step of finding, in the operating reference frame, the position of several anatomic points of a patient.

An object of the present invention is to provide a reference body fastening device which can be located by a localization system and which is easily installed.

An object of the present invention is to provide a device that can apply to a large series of patients.

An object of the present invention is to provide a device which has a good stability all along the intervention.

An object of the present invention is to provide a device which has a substantially determined position with respect to the anatomic structure on which it rests.

SUMMARY OF THE INVENTION

To achieve these objects, the present invention provides a method for readjusting the reference frame of a device placed on a patient during an intervention with respect to the reference frame of a pre-recorded three-dimensional image of this patient. The method includes the steps of:

a) placing on the patient a device applicable to several patients and having a predetermined position relation with the patient's anatomic structure;

b) finding the position of said device with respect to a localization system; and c) by means of the localization of said device and of the predetermined position relation of the device with the patient's anatomic structure, determining a relation between the reference frame of the device and the reference frame of said image.

According to an embodiment, the step of determining the relation between the reference frame of the device and the reference frame of said image includes the steps of:

determining, with respect to said device, the position of points belonging to the patient's anatomic surface, using iterative readjustment algorithms to determine in the pre-recorded image the position of this anatomic surface, these algorithms using the predetermined position relation of the device with the anatomic structure to begin their search, and determining a transfer array defining the relation between the reference frame of the device and the reference frame of said image.

According to an embodiment, in the case where the patient keeps a substantially stable position during the imaging, the readjustment algorithms use, whoever the patient, a single initial transfer array determined once and for all by means of said device.

According to an embodiment, the readjustment algorithms use a set of initial transfer arrays limited to the space of translations.

According to an embodiment, the readjustment algorithms use an initial transfer array and, in the case where said device enables determining the three rotation parameters of the initial transfer array, the three rotation parameters of the array are defined by choosing an arbitrary point on the patient's surface defined on the three-dimensional image, displaying this point according to cross-section and projection views, and asking an operator to designate this point in the reference frame of the device by means of a sensor.

According to an embodiment, the readjustment algorithms use an initial transfer array and, in the case where said device enables determining certain parameters of the initial transfer array, the other parameters are defined by performing a fine readjustment based on the admissible positions so calculated and only keeping the best relation.

The present invention also provides a fastening device that can apply to a wide series of patients and support a marking means; this device includes at least three bearings intended for resting upon an anatomic structure of the patient so that a predetermined position relation between the device and the anatomic structure can be established.

According to an embodiment, the device includes:

an element including a first V-shaped bearing intended for resting upon the nasion and two other bearings intended for resting upon the forehead above the eyebrows;

first and second moulds following the shape of the patient's ear conchas, intended for being respectively placed in one or the other of the patient's ears;

a holding bar for holding said element in a stable position, said holding bar including a central portion intended for resting upon the element and two branches intended for being coupled to said first and second moulds.

According to an embodiment, the device further includes sliding rings having rods for coupling said branches to said first and second moulds.

According to an embodiment, said element has a multiple-position notch system located between the first bearing and the two other bearings, the notch system being intended for receiving the central portion of the holding bar and for enabling setting of the device hold pressure.

According to an embodiment, the marking means includes two lateral plates oblique with respect to each other exhibiting reference elements.

According to an embodiment, the marking means further includes a front triangular plate having at least three holes and/or at least one calibration pin.

According to an embodiment, the device, applicable to a lumbar vertebra, includes two bearings intended for being placed on the back edge of the spinal crest and pliers with a jaw perpendicular to the straight line passing through said two bearings.

According to an embodiment, the device, applicable to a thoracic vertebra, includes two bearings intended for being placed on the back edge of the spinal crest and pliers with a jaw forming, with respect to the straight line passing through the two bearings, a predetermined angle defined by the level of the vertebra.

The present invention also provides a reference pin, usable in the method of the present invention or in cooperation with the device of the present invention; the reference pin includes:

a cylindrical tip having a given diameter D, intended for inserting into a hole drilled in a bone and substantially having the same diameter D, a flange supported by the cylindrical tip, and a marking means enabling localization of a reference point of the reference pin.

BRIEF DESCRIPTION OF THE DRAWINGS

The foregoing objects, features and advantages of the present invention will be discussed in detail in the following non-limiting description of specific embodiments in connection with the accompanying drawings.

Various embodiments of the present invention will now be described.

DETAILED DESCRIPTION OF THE DRAWINGS

FIGS. 1 to 5 illustrate a first embodiment of a device according to the present invention, usable for example in ENT surgery, neurosurgery, brain radiotherapy, and in oral surgery.

Figure 1:
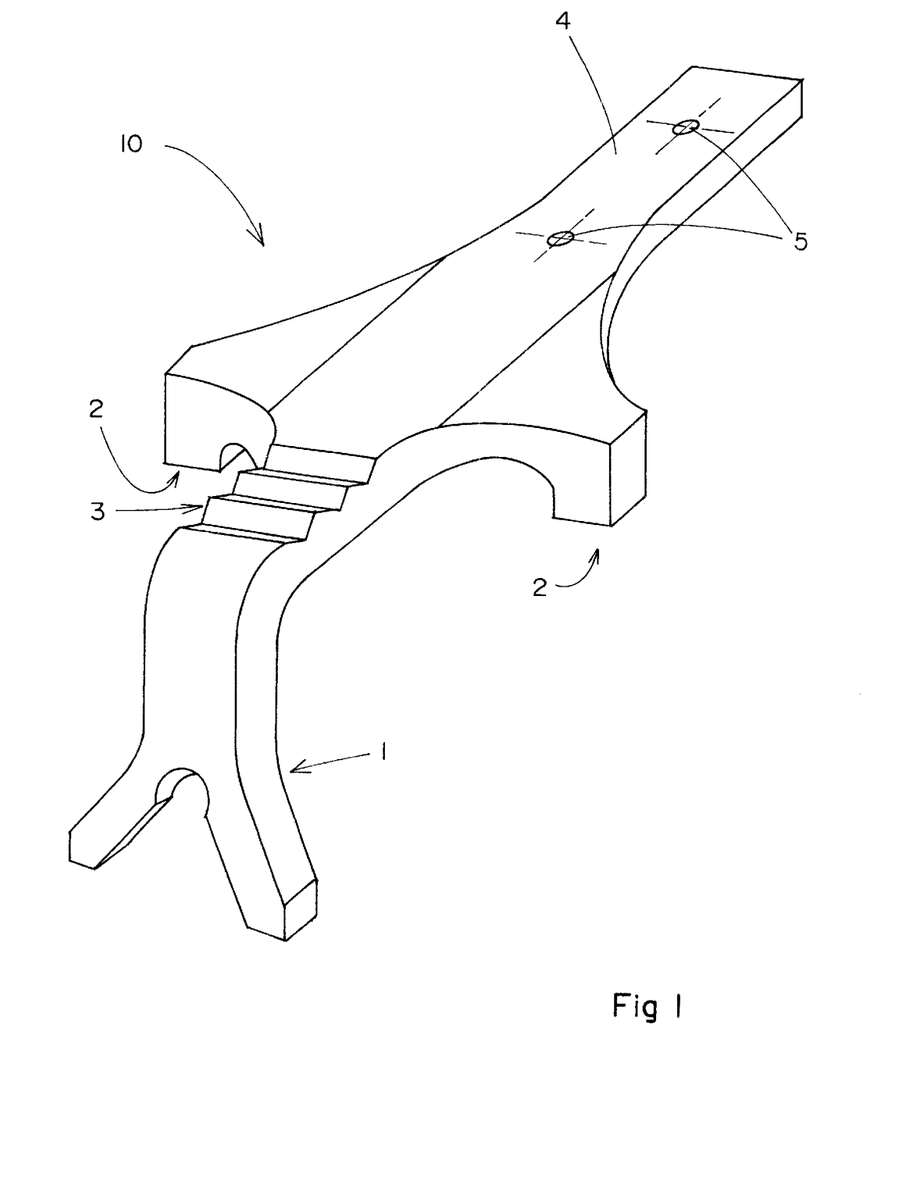
FIG. 1 is a perspective view of an element of a device according to the first embodiment of the present invention.

FIG. 1 shows an element 10 of this device. Element 10 of FIG. 1 has an elongated shape and has on one end a first bearing 1 intended for resting upon the nasion. This bearing is V-shaped and has, as on glasses, two lateral oblique surfaces ensuring a proper positioning at the level of the nose root. Element 10 then is curved and includes two other bearings 2. Bearings 2 are formed of slightly rounded surfaces and are intended for bearing against the forehead above the eyebrows. Further, the element of FIG. 1 has, between first bearing 1 and front bearings 2, a notch system 3 with several positions (three in the illustrated example), the function of which will be described hereafter. The element of FIG. 1 ends, in the example shown, with a rectilinear portion 4 including two fastening holes 5. These holes are intended for fastening by any fastening means, like screws, a marking means (not shown in FIG. 1), like for example a reference body carrying light-emitting diodes, this reference body enabling finding of the position of the device by a localization system associated with the operating chamber. Those skilled in the art should note that element 10 of FIG. 1 could intrinsically include the means enabling its localization in the operating chamber.

Figure 2:
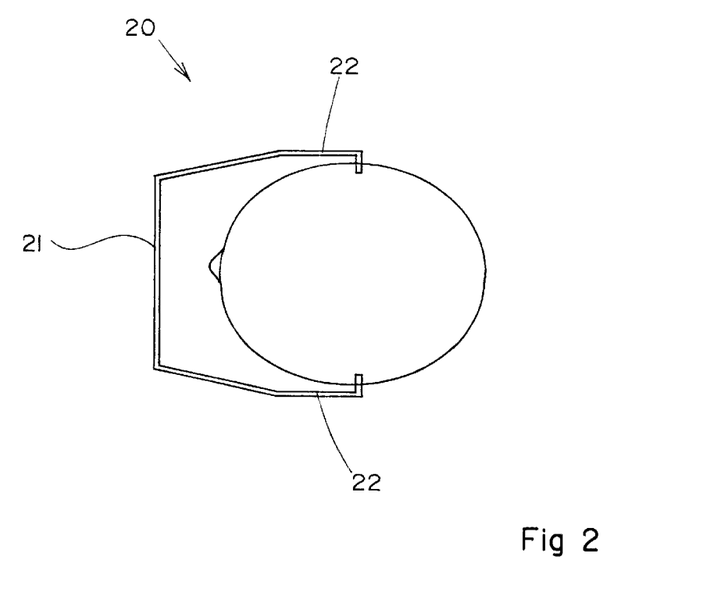
FIG. 2 is a top view of another element of the device according to the first embodiment of the present invention.

FIG. 2 illustrates a holding bar 20 intended for cooperating with element 10 to maintain it in a stable position on the patient. Holding bar 20 is roughly U-shaped and has a central portion 21 and two branches 22. FIG. 2 shows holding bar 20 applied to a patient's head and it can be seen that, in this embodiment, the ends of branches 22 are curved and insert into the patient's ears.

Figure 3:
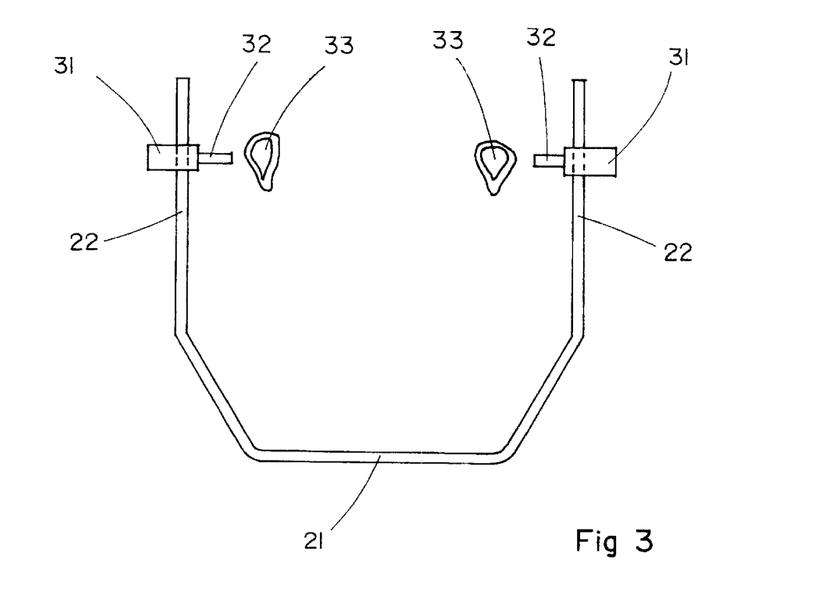
FIG. 3 illustrates an alternative of the element of FIG. 2, as well as other elements of the device according to the first embodiment of the present invention.

FIG. 3 shows an alternative embodiment of holding bar 20 in which branches 22 receive rings 31 ending in rods 32. Rings 31 can slide on branches 22 of the holding bar to enable a setting adapted to the patient's morphology. When the position of the rings is set, the rings are tightened on branches 22 by a tightening means (not shown) and rods 32 of the rings are inserted in the patient's ears.

The inserting of the curved ends of branches 22 of FIG. 2 or of rods 32 of FIG. 3 is not directly performed into the patient's ears, to avoid hurting him. Moulds 33 following the shape of the patient's ear conchas are made, for example in resin. These moulds are placed in the patient's ears and the ends of branches 22 or rods 32 of rings 31 insert into these moulds. Moulds 33 can easily be made for each patient but, in practice, three or four types of moulds are sufficient for a wide population, which results in savings of time and equipment.

Figure 4:
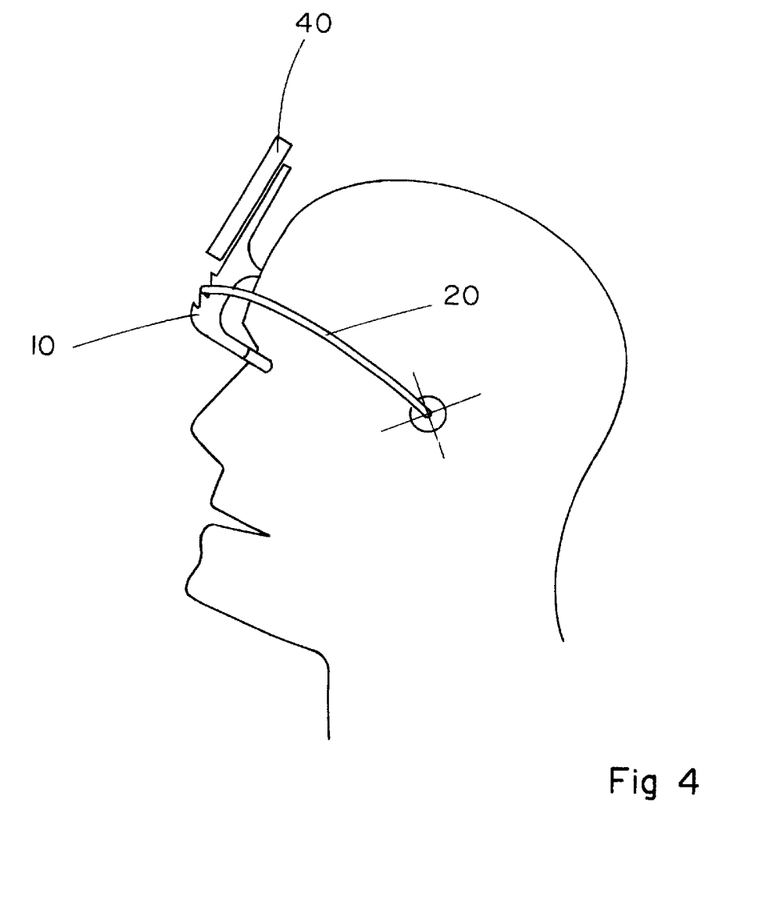
FIG. 4 is a representation of the device according to the first embodiment of the present invention applied to a patient.

FIG. 4 illustrates a device according to the first embodiment of the present invention positioned on a patient. It shows element 10 with its anatomic bearings, holding bar 20 with its ends coupled to the patient's ears. The central portion of holding bar 20 bears against one of the notches, here the median notch, of the multiple-position notch system of element 10 and enables maintaining element 10 in position while setting the hold pressure. Thus, element 10 is immobilized, without it being necessary to exert excessive tightening forces. Further, this drawing shows a marking means 40 attached to element 10 enabling finding the device in the operating chamber. Finally, it should be noted that the device is sufficiently thin and hollow to avoid disturbing the surgeon's action during the operation.

Figure 5A:
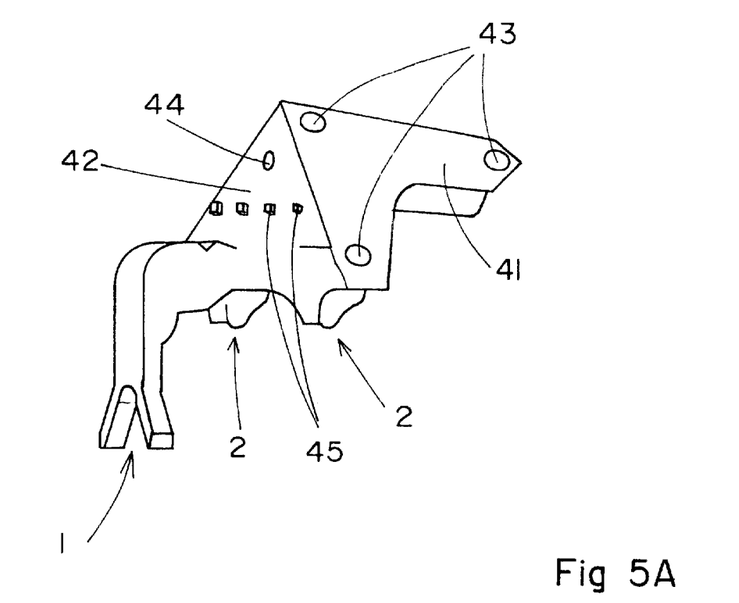
FIGS. 5A and 5B show a device according to the first embodiment of the present invention provided with a specific marking means.
Figure 5B:
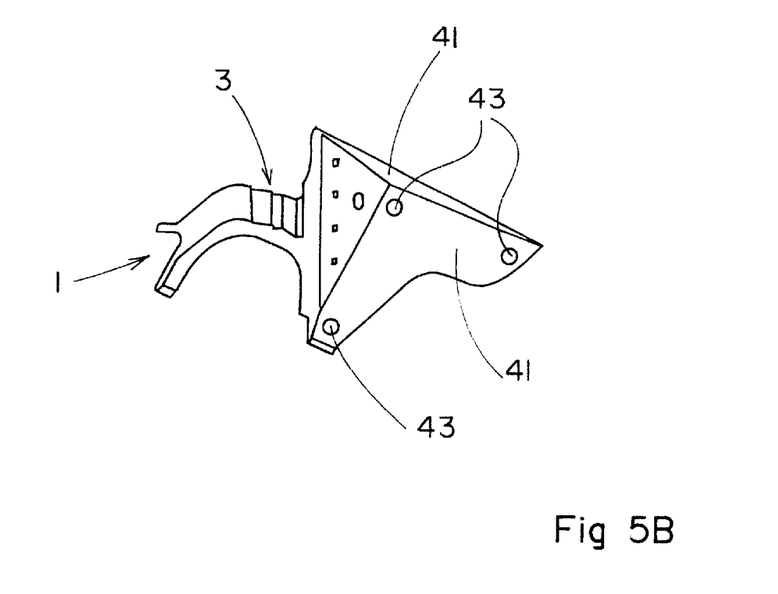

FIGS. 5A and 5B show two perspective views of a device according to the first embodiment of the present invention provided with a specific marking means. It shows element 10 with its bearings 1, 2; notch system 3 of element 10 is also shown. Here, the marking means supported by element 10 includes a support (not shown) on which are attached by any means, for example, magnetic means, two lateral plates 41 oblique with respect to each other. Lateral plates 41 include marking elements 43 such as reflective tags, locatable by the localization system. In the shown embodiment, the plates are provided with three circular holes and cover a precut reflective strip so that the plate acts as a mask only letting through the hole pattern. An advantage of such a marking means is that, whatever the patient's position, at least one of oblique plates 41 is always visible and easily detected by the localization system. The patient's head can thus be significantly moved, without being afraid that the localization system should loose track of the marking means. Further, this marking means includes a triangular front plate 42 that advantageously has one or several holes 43 and one or several pins 44 enabling calibration of tools.

The device described up to now applies to head surgery, especially ENT. The present invention is not limited to this field. Generally speaking, the present invention aims at devices applicable to various parts of the human body, finding a same position before and after disassembly, this position having a specific determined relation with respect to the neighboring anatomic structures.

Figure 6A:
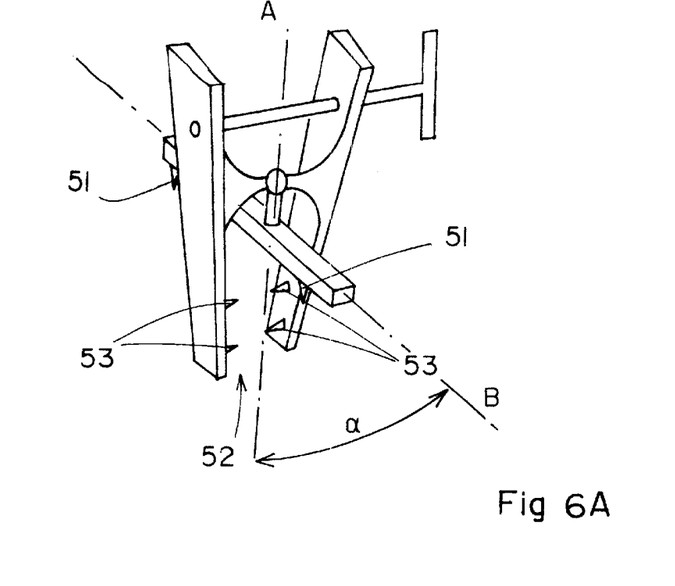
FIGS. 6A and 6B show two perspective views of a device according to a second embodiment of the present invention.
Figure 6B:
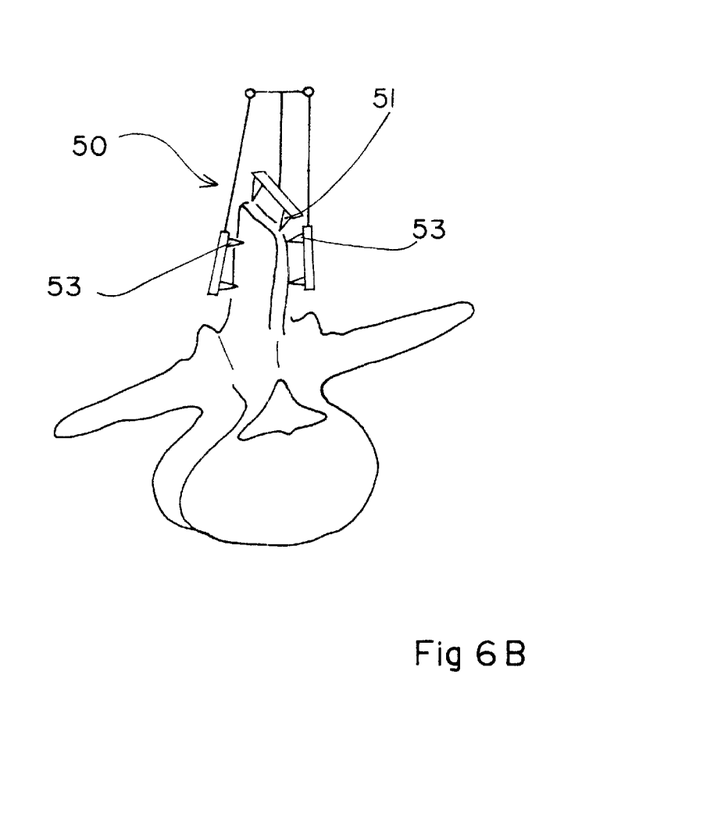

FIGS. 6A and 6B illustrate, as an example, another embodiment of the present invention. In this embodiment, a device according to the present invention is applied to a vertebra. The device includes two bearings 51 intended for being placed on the back edge of the spinal crest. A pair of jaw pliers 52 has conventional lateral bearings 53 and enables fastening of the device on the vertebra. Longitudinal axis A of jaw pliers 50 forms a given angle α with a straight line B passing through both bearings 51. In the case of a lumbar vertebra, the pair of jaw pliers is perpendicular to line B and angle α is equal to 90°. In the case of a thoracic vertebra, the pair of jaw pliers forms a predetermined angle depending on the level of the vertebra (for example 30°, 45°, etc.) with respect to line B. Due to the fact that bearings 51 rest upon a determined and well-defined portion of the vertebra, the device according to the present invention has a predetermined position relation with the anatomic structure and enables application of the method according to the present invention. FIG. 6B illustrates the device in position on a vertebra.

Figure 7A:
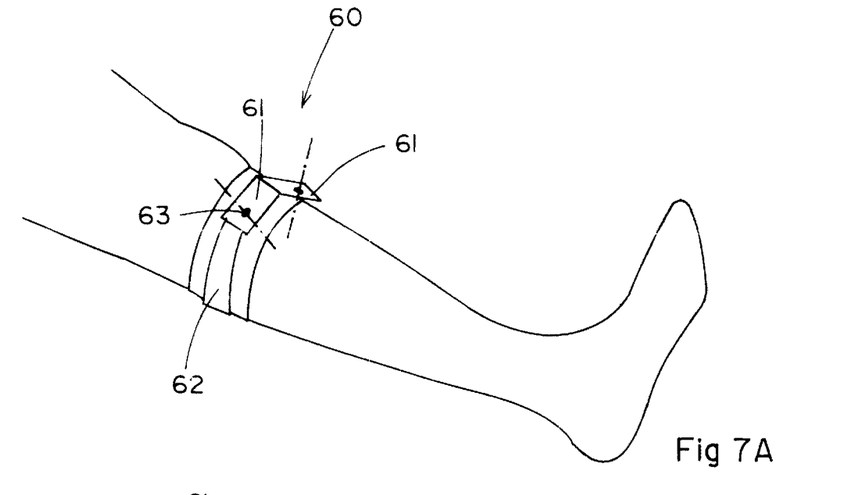
FIGS. 7A and 7B show a device according to another embodiment of the present invention.
Figure 7B:
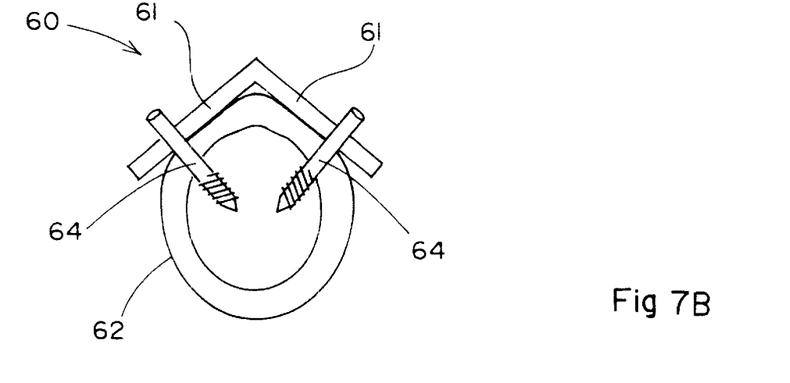

FIGS. 7A and 7B show a device according to another embodiment. Here, the device applies to a long bone, more specifically a tibia. In FIG. 7A, a device 60 formed by two portions 61 oblique with respect to each other is placed on the protrusion of the front external surface of the tibia and is tightened by a strap 62. One or two openings 63 enable insertion of the tubes through which pins can be attached. FIG. 7B shows a cross-section of the device with its fastening pins 64.

Each of the devices described hereabove has, as compared to the state of the art, different and/or a greater number of bearings, chosen to increase the stability and enable establishing a predetermined position relation between the device and an anatomic structure of the patient. Further, the devices of the present invention are applicable to a wide series of patients and have, whoever the patient, a predetermined position relation with the patient's anatomic structure, as indicated hereabove.

The present invention also provides a method for readjusting the reference frame of a device according to the present invention placed on a patient on the reference frame of a pre-recorded three-dimensional image of this patient. For this purpose, the fastening device according to the present invention is located and its predetermined position relation with the patient's anatomic structure is used to determine the relation between the reference frame of the device and the reference frame of the pre-recorded image.

Two cases occur, according to whether this predetermined position relation completely determines the patient's anatomic position or not.

In the first case, the device has a single position with respect to the patient's external anatomy. For example, such will be the case for the above-described device applicable to the head if the operator respects the provided bearings and if he ascertains that the nasal bearing comes to contact with the region between the eyebrows as high as possible on the nose. This situation provides the following advantages. First, it enables placing and removing the device at will, the device remaining in the same position with respect to the patient. Then, this single position can be predicted in the reference frame of the images by means of simulation tools. The position of the device with respect to the images during the intervention is then directly known. In this case, the predetermined position relation between the position of the device and the patient's position is sufficiently accurate to enable appropriate readjustment. It is thus avoided to perform the previous prior art step consisting of determining the position of a reference body with respect to the patient, which saves time and provides a better accuracy.

In the second case, the predetermined position relation between the device and the anatomic structure does not completely provide the position of the device with respect to the anatomic structure and only some of the parameters of the device position or their combinations are known. For example, the jaw pliers on the vertebra may slide in translation along the back edge of the spinal crest. The nasal bearing may also have a sliding motion of translation and slight rotation along the nose. In this case, the direct determination described hereabove only enables obtaining a rough and insufficient readjustment. The readjustment method must then be completed with a fine surface readjustment, to accurately determine the device position on the anatomic structure.

This determination, which amounts to finding the transfer array between two reference frames, can be performed in several ways.

As mentioned hereabove, fine state of the art readjustments conventionally use iterative readjustment algorithms to find transfer array M between the reference frame associated with the patient and the reference frame associated with the medical images. These algorithms establish a correspondence between points of the patient's anatomic surface determined with respect to the reference system attached to the patient and points of this same surface in the pre-recorded image. In prior art, an initial array, defined by the finding of several anatomic points in the localization system, has often been used as a starting point for the algorithms. This finding of the position of anatomic points takes time, but it is above all inaccurate and can be a source of significant errors. Thus, if the initial array is too distant from the searched array, the algorithms can converge to local minimum values and provide erroneous or even aberrant solutions. A solution to this problem would be to use exhaustive search algorithms, for which the surface readjustment convergence is carried out based on, for example, 206 initial arrays and where the best result is kept. The time required by the calculations is very long. The device according to the present invention provides a good approximation of the position of the considered surface of the patient, and enables obtaining an initial value of transfer array M which is very close to its final value. In other words, the rough readjustment mentioned hereabove is used to provide a starting base to the surface readjustment algorithms. Simpler algorithms can then be used, which converge rapidly in a reliable manner.

To determine the initial array, several modes are possible.

If, during the imaging examination, the patient is placed in a relatively constant anatomic position, it is possible to determine transfer array M between the two reference frames once and for all on any patient and store it in a file. For any new patient, this file is read from to form the initial array used by the readjustment algorithms, which is easy to implement and provides significant time-saving advantages.

If the patient, during the imaging examination, is only likely to have a translatory movement, two schemes are possible.

According to prior art, to have two surfaces correspond, 20 initial values will for example be used according to each of the 6 degrees of liberty. This corresponds to a computation with $20^6$ (64,000,000) initial arrays. When initial data are used due to the device of the present invention, for example to be limited to translations, there will then only be $20^3$ (8,000) initial arrays from which the fine readjustment will be performed, to only keep the best result.

In another scheme in the case of a translatory motion, the position of a surface point (for example, the most advanced surface point at the front or the most remote surface point at the back, or a point located in the middle of the nose) is automatically located in the image reference frame, based on a surface model constructed on the three-dimensional image; at the beginning of the intervention, the point defined by computer means is displayed on screen on different cross-section views and three-dimensional projections and the surgeon must designate this same point with a sensor located by the localization system to follow the translation of the point in the images.

Also, in an advantageous embodiment to determine the initial array, a computer processing of the pre-recorded image is used to mathematically define, on this image, the set of all the stable positions that can be taken by the fastening device of the present invention on the patient's anatomic surface. Geometric optimization methods used to solve mechanical element insertion problems may be used for this purpose. The set of stable positions is often reduced to a small number of positions (20, for example) located on a portion of trajectory or surface having a dimension of 1, 2, 3, or 4 instead of 6. Based on all the positions found by performing the fine readjustment based on the possible positions, the solution providing the best results in terms of residual error is kept.

Eventually, it may sometimes be desired to know with a great precision the position of the device according to the present invention with respect to the patient. It may also, after having removed the device, be desired to place it back exactly at the same position as previously. In this case, another reference body having an entirely stable position with respect to the patient's anatomic structure may be placed on the patient in addition to one of the previously-described fastening devices, and the position of the device of the present invention may be found or checked with respect to this second reference body.

For example, in the case of head surgery, a dental casting of the previously-described type may be used and the position of the device according to the present invention may be found with respect to this casting. The dental casting is then considered as an absolute reference with respect to the patient since its position theoretically is more stable. Since the dental casting is bulky, it may be placed for example at the beginning of the intervention to define the exact position of the device of the present invention, then removed during the intervention. It may be replaced each time a slight misadjustment of the device according to the present invention is suspected and used for a possible correction.

At least three punctual structures may also be fixedly placed on the patient's anatomic structure and the position of these reference points may be located at the beginning of the intervention. During the intervention, when the user suspects a possible displacement of the fastening device of the present invention or when he desires to determine its position with a great accuracy, the position of these reference points is determined and a readjusttent is performed between the device reference frame and the reference points. The punctual structures may conventionally be marks drawn on the skin, or specific anatomic points such as dental junctions, or else material structures affixed to the anatomic structure.

Figure 8:
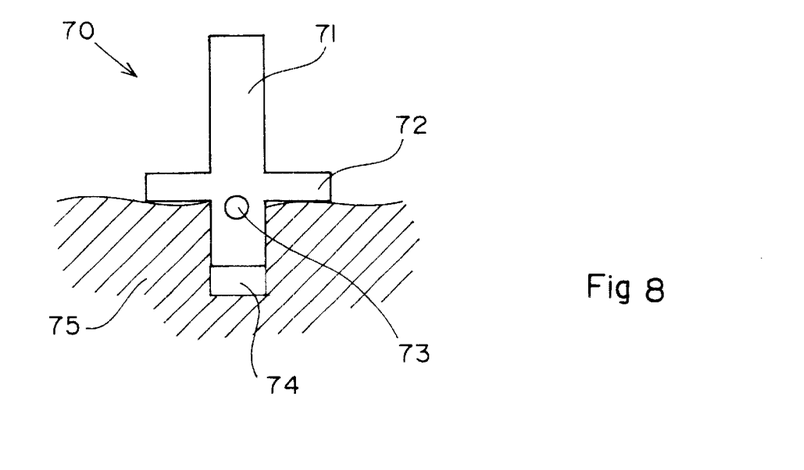
FIG. 8 shows a reference pin in a usable position in the present invention.

Advantageously, the punctual structures may be small holes of a diameter D of approximately 1 millimeter drilled in a bone and which are detected by the localization system with a reference pin of identical diameter D. FIG. 8 illustrates such a reference pin. Reference pin 70 includes a cylindrical portion 71 of diameter D and a flange 72 supported by the cylindrical tip. It also includes a marking means (not shown) enabling determination of the position of a reference point 73 by the localization system. When used, the reference pin is inserted in a hole of same diameter 74 drilled in a bone 75; flange 72 limits the penetration of the cylindrical tip into the bone and enables placing with accuracy reference point 73 on the bone surface. This arrangement is advantageous and can be used in cooperation with one of the foregoing devices or in the method of the present invention.

Although the present invention has been described in the context of a limited number of embodiments, the present invention is not limited to these specific embodiments and is likely to have various alternatives and modifications which will occur to those skilled in the art.

What is claimed is:

1. A fastening device that can apply to a wide series of patients, including at least three bearings intended for resting upon an anatomic structure of the patient so that a predetermined position relation between the device and the anatomic structure can be established and a marking means supported by said fastening device, wherein said fastening device includes:

an element including a first one of the at least three bearings, the first one of the at least three bearings being V-shaped and intended for resting upon a nasion of the patient and second and third ones of the at least three bearings intended for resting upon a forehead of the patient above eyebrows of the patient;

first and second moulds following a shape of the patient's ear conchas, intended for being respectively placed in one or the other of the patient's ears;

a holding bar for holding said element in a stable position, said holding bar including a central portion intended for resting upon the element and two branches intended for being coupled to said first and second moulds.

2. The device of claim 1, further including sliding rings having rods for coupling said branches to said first and second moulds.

3. The device of claim 1, wherein said element has a multiple-position notch system located between the first one of the at least three bearings and the second and third ones of the at least three bearings, the notch system being intended for receiving the central portion of the holding bar and for enabling setting of the device hold pressure.

4. The device of claim 1 wherein the marking means includes two lateral oblique with respect to each other exhibiting reference elements.

5. The device of claim 4 wherein the marking means further includes a front triangular plate having at least three holes.

6. The device of claim 4 wherein the marking means further includes a front triangular plate having at least three holes and at least one calibration pin.

7. The device of claim 4 wherein the marking means further includes a front triangular plate having at least one calibration pin.

8. A method for readjusting a reference frame of a device placed on a patient during an intervention with the reference frame of a pre-recorded three-dimensional image of this patient, including the steps of;

a) placing on the patient the device of any of claims 1 to 5:

b) finding a position of said device with respect to a localization system; and c) by means of the localization of said device and of a predetermined position relation of the device with a patient's anatomic structure, determining a relation between the reference frame of the device and the reference frame of said image, wherein the step of determining the relation between the reference frame of the device and the reference frame of said image includes the steps of:
- determining, with respect to said device, the position of points belonging to the patients anatomic surface,
- using iterative readjustment algorithms to determine in the pre-recorded image the position of this anatomic surface,
- these algorithms using the predetermined position relation of the device with the anatomic structure to begin their search, and
- determining a transfer array defining the relation between the reference frame of the device and the reference frame of said image.

9. The method of claim 8, wherein, in the case where the patient keeps a substantially stable position during the imaging, the readjustment algorithms use, whoever the patient, a single initial transfer array determined once and for all by means of said device.

10. The method of claim 8, wherein the readjustment algorithms use a set of initial transfer arrays limited to the space of translations.

11. The method of claim 8, wherein the readjustment algorithms use an initial transfer array and, in the case where said device enables determining the three rotation parameters of the initial transfer array, the three rotation parameters of the array are defined by choosing an arbitrary point on the patient's surface defined on the three-dimensional image, displaying this point according to cross-section and projection views, and asking an operator to designate this point in the reference frame of the device by means of a sensor.

12. The method of claim 8, wherein the readjustment algorithms use an initial transfer array and, in the case where said device enables determining certain parameters of the initial transfer array, the other parameters are defined by performing a fine readjustment based on the admissible positions so calculated and only keeping the best relation.

* * * * *